US 6,714,824 B1

(12) United States Patent
Ohta et al.

(10) Patent No.: US 6,714,824 B1
(45) Date of Patent: Mar. 30, 2004

(54) UNIVERSAL ELECTRODE SYSTEM AND METHODS OF USE AND MANUFACTURE

(75) Inventors: Seiya Ohta, NewCastle, WA (US); Thomas Allen Solosko, Issaquah, WA (US); Hans Patrick Griesser, Bainbridge Island, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/579,962

(22) Filed: May 26, 2000

(51) Int. Cl.[7] ................................................ A61N 1/04
(52) U.S. Cl. ...................................................... 607/142
(58) Field of Search ......................... 607/142; 600/372, 600/382–393

(56) References Cited

U.S. PATENT DOCUMENTS

| | | |
|---|---|---|
| 4,419,998 A | 12/1983 | Heath |
| 4,483,103 A | 11/1984 | Bickel |
| 4,653,503 A | 3/1987 | Heath |
| 4,681,112 A | 7/1987 | Jones et al. |
| 4,807,621 A | 2/1989 | Hagen et al. |
| 4,852,585 A | 8/1989 | Heath |
| 4,895,169 A | 1/1990 | Heath |
| 4,955,381 A | 9/1990 | Way et al. |
| 4,979,517 A | 12/1990 | Grossman et al. |
| 5,080,099 A | 1/1992 | Way et al. |
| 5,137,458 A | 8/1992 | Ungs et al. |
| 5,295,482 A | 3/1994 | Clare et al. |
| 5,330,526 A | 7/1994 | Fincke et al. |
| 5,352,315 A | 10/1994 | Carrier et al. |
| 5,466,244 A | 11/1995 | Morgan |
| 5,520,683 A | 5/1996 | Subramaniam et al. |
| 5,571,165 A | 11/1996 | Ferrari |
| 5,617,853 A | 4/1997 | Morgan |
| 5,967,817 A | 10/1999 | Greenstein |
| 6,101,413 A  * | 8/2000 | Olson et al. .................. 607/5 |
| 6,240,323 B1 * | 5/2001 | Calenzo et al. ............. 600/372 |

OTHER PUBLICATIONS

"Improving Survival from Sudden Cardiac Arrest: The 'Chain of Survival' Concept" Circulation 83:1832–1847 (1991).

* cited by examiner

*Primary Examiner*—Jeffrey R. Jastrzab

(57) ABSTRACT

Electrodes are capable of delivering synchronized cardioversion and pacing energy pulses as well as defibrillation energy pulses to a patient. The electrodes are also appropriate for use with an automatic or semi-automatic external defibrillator (AED) as well as defibrillators capable of cardioversion and manual defibrillators. The electrodes have a plurality of conductors sized for delivering electrotherapy to patients of different sizes. Preferably, conductors can be used singly or in combination for therapy. The electrodes may also be separated to form electrodes of smaller dimension for application to a smaller patient.

24 Claims, 5 Drawing Sheets

UNIVERSAL ELECTRODE SYSTEM AND METHODS OF USE AND MANUFACTURE

BACKGROUND OF THE INVENTION

1. Field of the Invention

This invention relates generally to medical electrode systems. In particular, the electrodes of this invention are capable of universal application to patient's of any size. The electrodes of this invention are appropriate for use with defibrillators, including an automatic or semi-automatic external defibrillator ("AED") and defibrillators capable of cardioversion or external pacing.

2. Description of the Prior Art

Cardiac arrhythmias treatable with an electric shock can be further categorized as arrhythmias treated by a defibrillation energy shock or arrhythmias treated by a synchronized cardioversion energy shock. Electric shocks are typically delivered by defibrillators or cardioverters. Many devices capable of delivering a defibrillation shock are also capable of delivering synchronized cardioversion shocks. Defibrillation is typically used to treat ventricular fibrillation ("VF") and pulseless ventricular tachycardia ("VT"), while cardioversion is typically used to treat hemodynamically stable ventricular tachycardia ("VT with pulse"), paroxysmal supraventricular tachycardia ("PSVT"), atrial fibrillation ("AF") and atrial flutter. More detailed information about electrocardiography and the various types of heart rhythms may be obtained from Wagner "Marriott's Practical Electrocardiography," 9th Ed. (1994).

One frequent consequence of heart attacks is the development of cardiac arrest associated with heart arrhythmias, such as VF. This abnormal heart rhythm is caused by an abnormal and chaotic electrical activity in the heart. During VF the heart cannot pump blood effectively. VF is treated by applying a defibrillation shock to the patient's heart through the use of a defibrillator. Defibrillation clears the heart of the abnormal electrical activity and allows the heart's natural pacemaker areas to restore normal function. Because blood is no longer pumping effectively during VF, the chance of surviving sudden cardiac arrest decreases with time. Quick response to sudden cardiac arrest by administering a defibrillating shock as soon as possible after the onset of VF is therefore often critically important.

VT is an arrhythmia originating in the ventricles, and is usually defined as having a heart rate of >100 beats/minute in an adult. VT can result in a significant health risk, since the ability of the heart to pump adequate blood is compromised. As a result, blood pressure falls. Hemodynamically stable VT is typically treated using synchronized energy pulses known as cardioversion that are delivered in a standard sequence of, for example, 100, 200, 300 and 360 J. Although in some situations, pulses may begin with as little as 50 J. Hemodynamically unstable VT is typically treated with unsynchronized shocks. The most current protocol information can be obtained from the American Heart Association ("AHA"). The protocol information described herein can be found in "Improving Survival from Sudden Cardiac Arrest: The 'Chain of Survival' Concept" *Circulation* 83:1832–1847 (1991).

Increasing the number of potential defibrillator operators who are trained in the proper use of an external defibrillator increases the likelihood that a trained defibrillator operator will be available during an emergency and thus could ultimately reduce the time to defibrillator deployment. As the number of potential operators increases, however, it becomes increasingly important to ensure that defibrillator electrode pads of an appropriate size are available to treat the patient.

What is needed is an electrode system that is easily adaptable to the size of the patient.

SUMMARY OF THE INVENTION

This invention describes an electrode system that is easily adaptable to the size of the patient. This invention also describes methods of manufacture of an electrode system and methods of use.

This invention describes a disposable medical electrode pad comprising: a conductive gel layer having two surfaces each with a surface area; a single, separable conductive layer with a first conductive electrode section or area having two surfaces each with a surface area wherein one surface of the conductive electrode layer is adhered to one surface of the conductive gel layer and wherein the surface area of the first conductive layer is less than 100 $cm^2$; a second conductive electrode layer having two surfaces each with a surface area wherein one surface of the conductive electrode layer is adhered to one surface of the conductive gel layer and wherein the surface area of the second conductive layer is less than 150 $cm^2$; conductors in communication with the first and second conductive electrode layers wherein the conductors selectively deliver therapy through the first or second conductive electrode layer; and a dielectric layer. The surface area of the first conductive layer may be less than 75 $cm^2$ or 50 $cm^2$. Additionally, the surface area of the second conductive electrode layer may be less than 100 $cm^2$ or 75 $cm^2$. A third conductive electrode layer may also be provided in communication with the first and second conductive electrode layers. When a third conductive layer is provided, it ideally has a surface area of less than 40 $cm^2$. Any of these electrode pads are capable of delivering pulses of electrical energy, such as defibrillation pulses, cardioversion pulses, or pacing pulses. As configured, the first conductive electrode element is removable from the second electrode element and, when applicable, the third conductive element is removable from the first and second electrode elements. The gel layer may be contiguous, separated into first and second gel sections, or fairly contiguous with one or more sets of perforations along a length. The foam backing can similarly be contiguous, comprised of multiple sections or feature one or more sets of perforations along its length. A release liner may also be attached to one side of the gel layer. The release liner may be contiguous, comprised of multiple sections, or feature one or more sets of perforations along its length.

Alternatively, the disposable medical electrode pad may comprise: a first conductive gel layer having two surfaces each with a surface area; a second conductive gel layer having two surfaces each with a surface area; a conductive electrode layer having two surfaces each with a surface area wherein one surface of the conductive electrode layer is adhered to one surface of the conductive gel layer and wherein the surface area of the first conductive layer is less than 150 $cm^2$; conductors in communication with the conductive electrode layer; and a dielectric layer. In this embodiment, the conductive electrode layer may further comprise a first conductive electrode layer and a second conductive electrode layer. The surface area of the first conductive electrode layer is less than 75 $cm^2$ or 50 $cm^2$. The surface area of the second conductive electrode layer is less than 100 $cm^2$ or 75 $cm^2$. Additionally, a third conductive electrode layer in communication with the first and second conductive electrode layers. Where a third conductive layer is provided, its surface area is less than 40 cm². These electrode pads are also capable of delivering pulses of electrical energy, such as defibrillation, cardioversion or pacing. In this construction, the first conductive electrode element is removable from the second electrode element and, when applicable, the third conductive electrode element is removable from the first and second electrode element. The dielectric layer can be formed from a first dielectric layer and a second dielectric layer or the dielectric layer may be perforated along its length. A release liner may also be attached to one side of the gel layer. The release liner may be contiguous, comprised of multiple sections, or feature one or more sets of perforations along its length.

In another alternative, the disposable medical electrode pad comprises: a conductive gel layer; a conductive electrode layer having two surfaces each with a surface area wherein one surface of the conductive electrode layer is adhered to one surface of the conductive gel layer and wherein the surface area of the first conductive layer is less than 150 cm²; conductors in communication with the conductive electrode layer; a first dielectric layer; and a second dielectric layer. The conductive electrode layer may further comprise a first conductive electrode layer and a second conductive electrode layer. In that case, the surface area of the first conductive electrode layer may be less than 75 cm² or more preferably less than 50 cm²; and the second conductive layer is less than 100 cm² or more preferably less than 75 cm². As with the previous embodiments, a third conductive electrode layer in communication with the first and second conductive electrode layers. In that case, the surface area of the third conductive electrode layer is less than 40 cm². These electrode pads are suitable for delivering pulses of electrical energy. These pulses include, defibrillation, cardioversion and pacing. In this construction, the first conductive electrode element is removable from the second electrode element and, when applicable, the third conductive electrode element is removable from the first and second electrode element. The gel layer may be contiguous, formed from a first gel layer and a second gel layer, or may be perforated along its length. A release liner may also be attached to one side of the gel layer. The release liner may be contiguous, comprised of multiple sections, or feature one or more sets of perforations along its length.

The invention also contemplates a method of using a disposable medical electrode pad comprising: determining the physiological size of a patient; determining whether to remove a portion of a conductive electrode layer from an electrode pad prior to applying the electrode pad to the patient; applying the electrode pad to the patient; and monitoring the patient's condition. Further, the step of: removing a portion of the conductive electrode layer from the electrode pad may also be performed where an electrode with a smaller surface area is desired. In operation, this method of using the electrode enables the device to deliver defibrillation, cardioversion or pacing pulses.

The invention also includes methods of manufacturing the electrodes. In one method of manufacture, the steps of: cutting a layer of conductive gel to a desired shape; cutting a layer of conductive element to a desired shape; carefully registering the conductive gel layer and the conductive electrode layer; connecting a wire to the conductive electrode layer; and adhering the registered gel and conductive element to each of a plurality of dielectric layers.

In another method of manufacturing, the electrodes are made by: cutting a layer of conductive gel into a plurality of desired shapes; cutting a layer of conductive element to a desired shape; carefully registering the conductive gel layers and the conductive electrode layer; connecting a wire to the conductive electrode layer; and adhering the registered gel and conductive element to a dielectric layers.

In yet another method of manufacturing, the electrodes are made by: cutting a layer of conductive gel to a desired shape; cutting a layer of conductive element into plurality of desired shapes; carefully registering the conductive gel layer and the conductive elements; connecting wires to the conductive electrode layers; and adhering the registered gel and conductive element to one or more dielectric layers.

DESCRIPTION OF THE PREFERRED EMBODIMENTS

As used herein "electrode pad" refers to the completed electrode pad assembly that is attached to the patient. Further, "conductive electrode elements," "conductive elements," "electrode elements" and "elements" refer to the sub-components forming the conductive components of the electrode pad.

Figure 1:
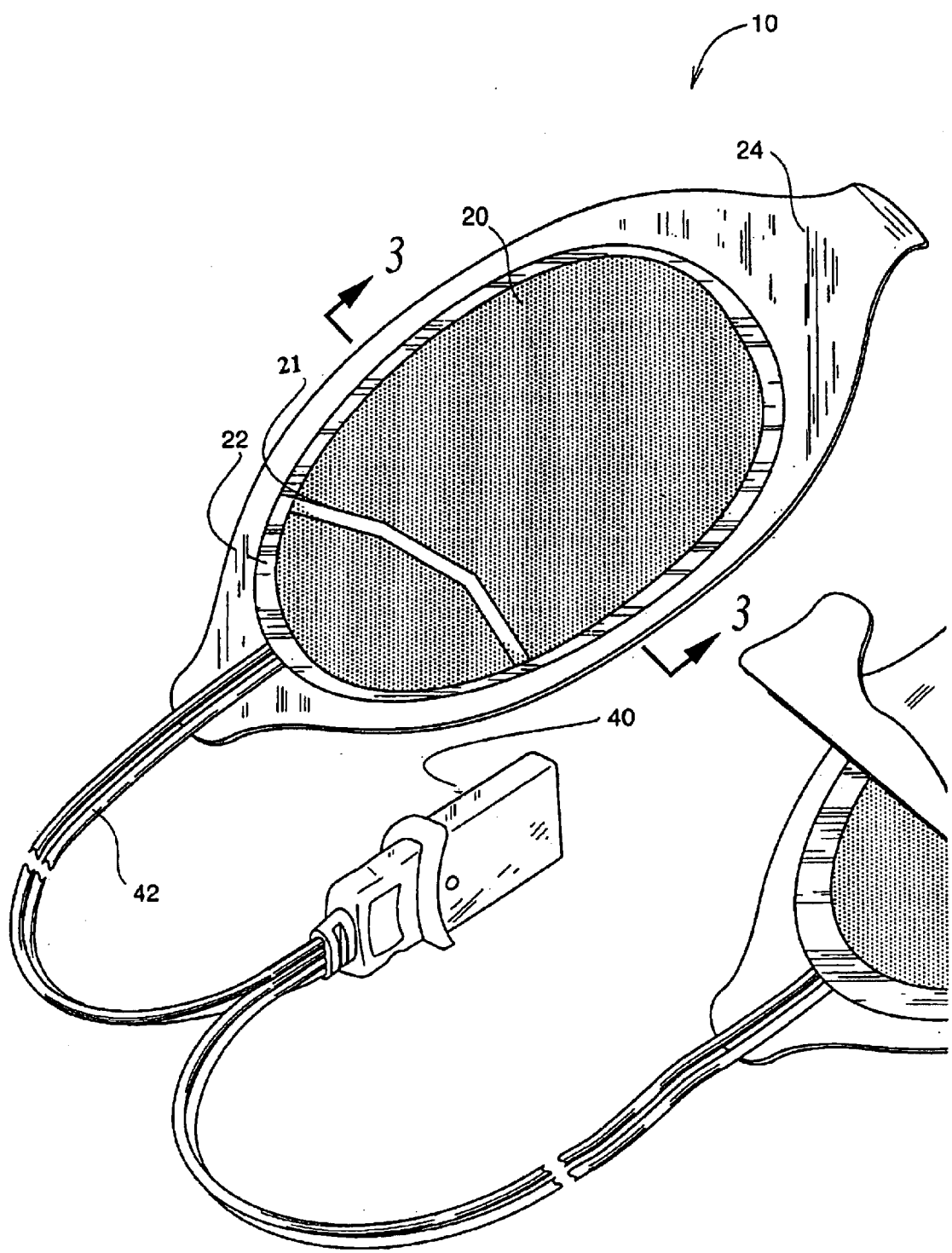
FIG. 1 is a bottom elevational view of an electrode system according to an embodiment of this invention wherein the electrode has two conductive elements.

FIG. 1 is a bottom elevational view of an electrode configuration according to an embodiment of this invention. As shown in FIG. 1, the electrode 10 has a single, separable conductive element 20 that can be separated into two or more sections 21, 22, together comprising a conductive contact area of 50 to 160 cm². In alternative embodiments, the conductive elements 21, 22 may be partially connected as a result of perforations along a length.

In the embodiment shown in FIG. 1, the size ratio between the outer conductive element 21 and the inner conductive element 22 is such that the surface area of the inner conductive element 22 is of a size appropriate for delivering defibrillation therapy to a child or infant patient and the combination of the outer conductive element 21 and inner conductive element 22 is of a size appropriate for delivering defibrillation therapy to an adult. Thus, for example, the size of the inner separated conductive element 22 would be, for example, 50 cm², the size of the separated outer conductive area 21 would be 100 cm², and the size of the combined inner conductive area 22 and the outer conductive area 21 would be 150 cm². The 50 cm² inner conductive area 22 would be used to deliver electrotherapy to an infant or pediatric patient and the 15 cm² combined conductive area would be used to deliver electrotherapy to an adult.

Figure 2:
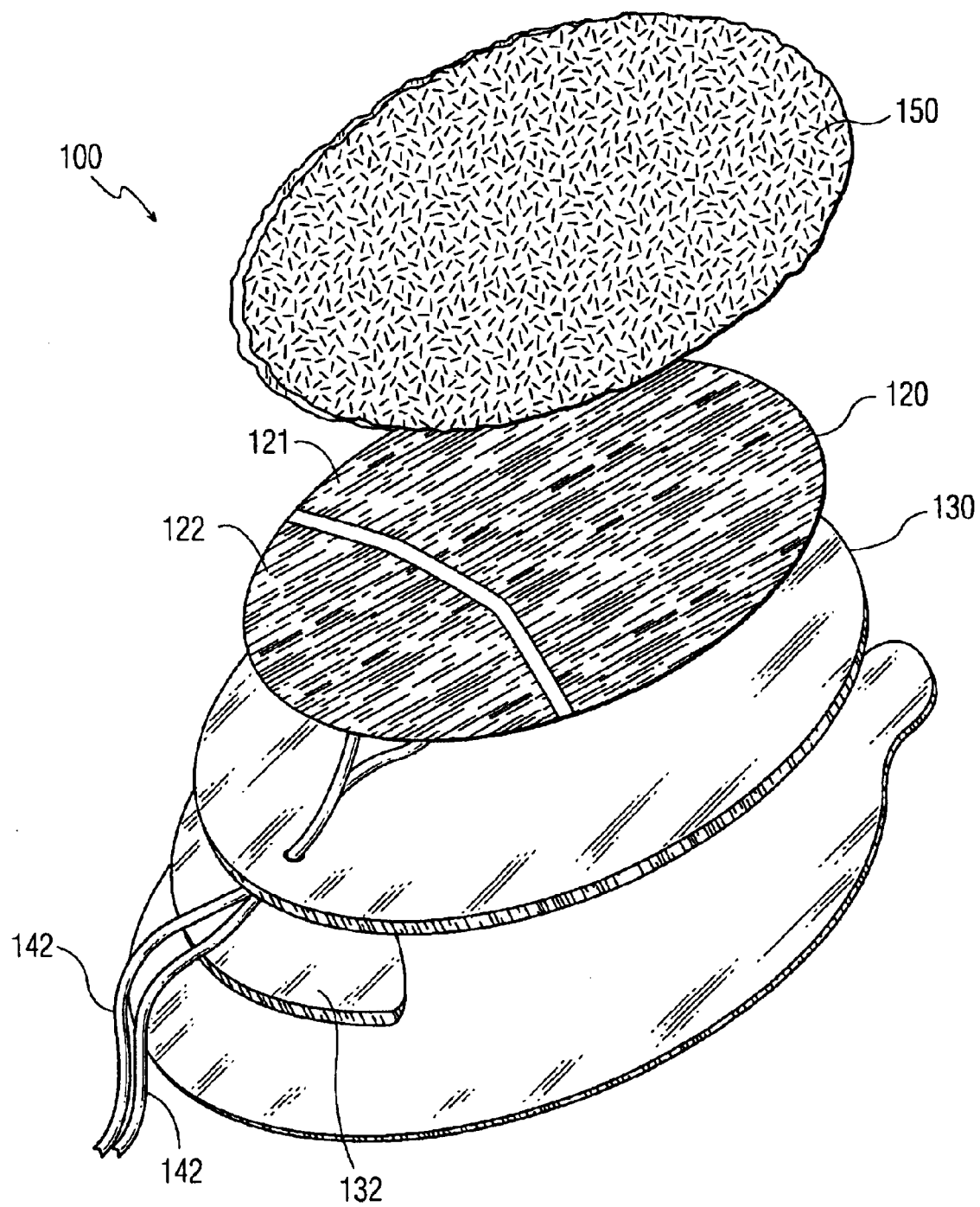
FIG. 2 is an expanded bottom elevational view of the electrode system of FIG. 1.

Referring to FIGS. 1 and 2, the conductive area 121, 122 has a dilectric backing layer 130 on one side and a conductive gel layer 150 on the other side as discussed in more detail below. The conductive layer 120, dielectric layer 130 and gel layer 150 together from the electrode pad 10. The electrode pad 10 is electrically connected to an interface 40 by wires 42. The interface 40 is, for example, an adapter for connecting the electrode assembly to a defibrillator. Further information about connector assembly is an available in U.S. Pat. No. 5,967,817 to Greenstein for Medical Connector Apparatus, the specification of which is incorporated herein.

In yet another embodiment, a single element separable into three conductive elements could be used. In one example, the three separable conductive elements are nested (i.e., a first conductive area surrounded by a second conductive area surrounded by a third conductive area). Although, as will be appreciated by those of skill in the art, nesting of the conductive elements is not necessary to practice the invention, as long as the combination of surface areas of the conductive elements are effective for the application. In this scenario, the first inner most separable conductive element would be sized for infants. The combination of the inner most conductive element with a middle conductive element would be sized for children (i.e., under 8 years of age). Finally, the combination of all three elements (inner, middle and outer) would be sized for adult therapy. Alternatively, each separable element could be independently sized for therapy delivery. In this case, the inner most conductive element would be sized for infants, the middle conductive element would be sized for children, and the third element would be sized for adults.

In the embodiment shown in FIG. 1, the inner conductive element 22 is used to deliver therapy to an infant or a child. The inner conductive element 22 may be used in cooperation with the outer conductive element 21 to deliver defibrillation energy to an adult.

In operation, the electrode 10 of FIG. 1 enables a defibrillator to deliver either pediatric therapy or adult therapy through one set of electrodes. Although the defibrillator can deliver pediatric therapy or adult therapy through one set of electrodes, when using a manual defibrillator the operator would still be required to choose the appropriate energy level.

In another solution, multiple conductive elements 20 of different sizes may be provided in a stacked arrangement (i.e., one on top of another). For example, a first conductive element of less than 160 $cm^2$ (appropriate for adult defibrillation) would be removably adhered to a second conductive element of less than 75 $cm^2$ (appropriate for child defibrillation). Additionally the first and second conductive elements could be removably adhered to a third conductive element of less than 40 $cm^2$ (appropriate for infant defibrillation). If such an arrangement is used, a conductive gel layer (such as 50) is provided between each layer. Thus, for example, if the stack is oriented so that the largest layer is the first layer exposed when the release liner is removed, the user may remove one or more of the removably adhered layers to expose a conductive electrode layer and corresponding gel layer of a desired size.

FIG. 2 shows an expanded bottom elevational view of the electrode of FIG. 1. In this embodiment, the electrode pad 10, is formed from a substrate, such as a flexible foam backing 130. The substrate has a conductive electrode element 120. The conductive element may be formed from two or more sub elements 121, 122 at the time of manufacture or may result at the time of deployment when the user alters the size of the electrode assembly. The electrode elements are formed, for example, from a piece of metal foil, and attached to the substrate with medical grade adhesive.

Suitable metal foil would be, for example, 2mil Tin. The conductive electrode element 120 is electrically connected to one or more lead wires 142 between the foam backing layer 130 and the conductive electrode element 120 on the upper surface of the conductive electrode element 120.

The lower surface of the conductive electrode element 120 is covered with one or more layers of conductive gel 150. A suitable conductive gel 150 would be, for example, an RG 63T hydrogel. A gap may exist in the gel layer depending upon the manufacturing process employed as discussed below.

An additional piece of flexible foam 132 may be further provided at the location where the electrical connection 142 attaches to electrode pad 100.

Figure 3:
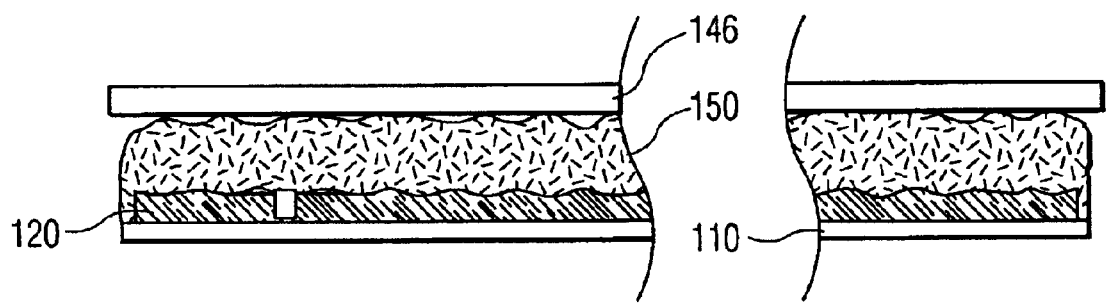
FIG. 3 is a cross-sectional view of the electrode system of FIG. 1 along the lines 3—3.
Figure 4:
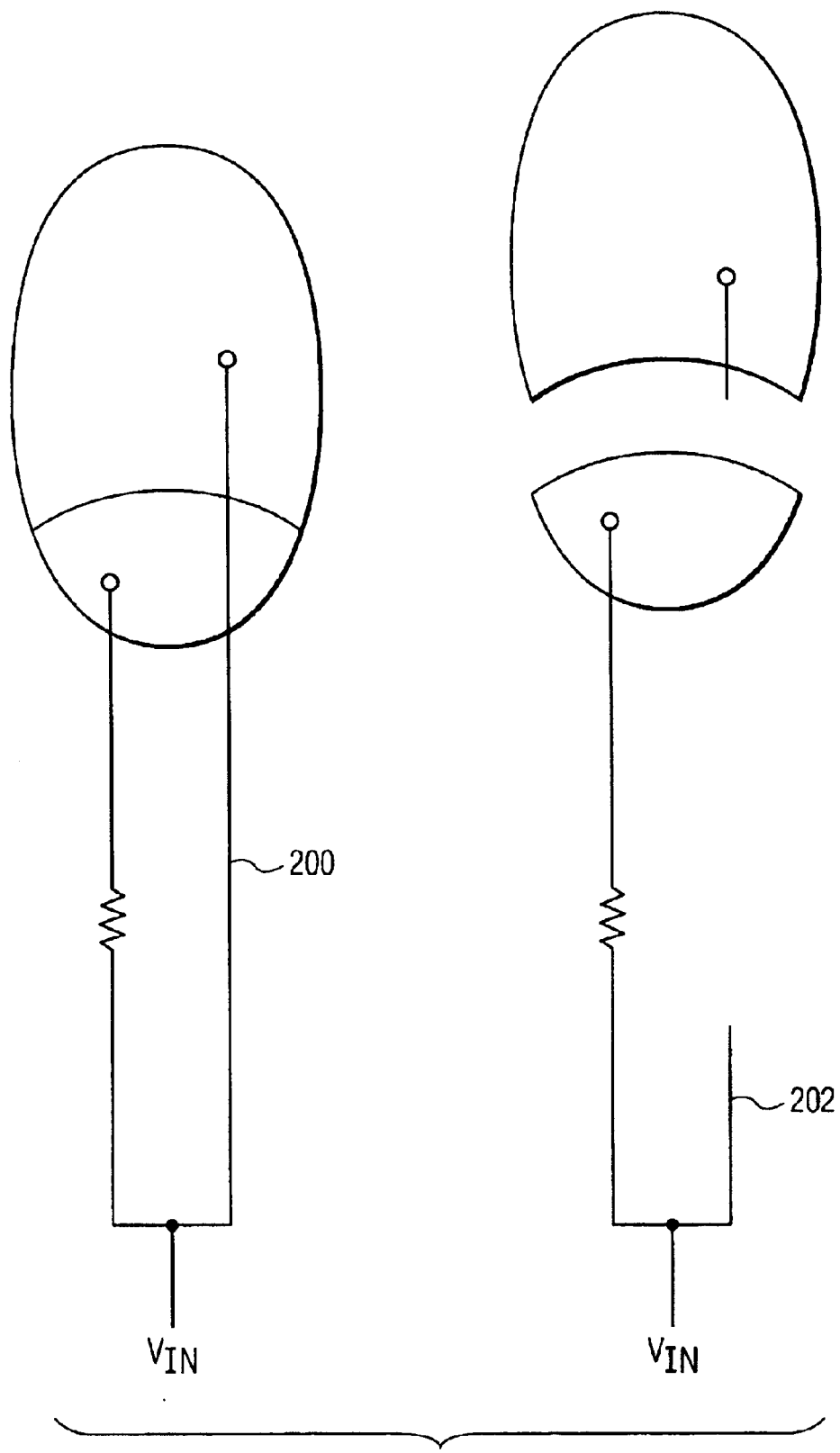
FIG. 4 is a bottom elevational view of an electrode system according to an embodiment of this invention showing the attenuation of energy delivered when a removable section of the electrode is removed.

The conductive gel layer 150 of the electrode pad 100 may be attached to the silicone coated side of a releasing surface (shown in FIG. 3).

In one method of manufacturing the electrode shown in FIGS. 1 and 2, the dielectric backing material 130, such as foam, is die-cut into two or more pieces. The pieces are then placed into a vacuum fixture to hold them into position. A solid conductive layer 120, such as tin, is laminated directly on top of the die-cut foam pieces. Preferably, the conductive layer 120 is tearable. Thereafter a gel registration fixture, which is connected directly to the vacuum fixture to achieve consistant registration, is placed on top of the conductive layer.

A variety of gels may be used in manufacturing the electrode. For example, gel that is pre-formed into sheets is appropriate. When sheet gel is used, film that is adhered to the gel layer for protection is removed from one side of the gel at which point the now exposed side of the gel layer is adhered to the final release liner 160. Thereafter the remaining film layer is removed from the gel and the gel-release liner assembly is placed into the gel registration fixture. At this point the gel registration fixture is removed and a roller is passed over the gel sections to ensure good bond to the tin layer.

As other methods of manufacturing are employed variations the final construction of the electrodes will result. For example, as mentioned above other gels are suitable for the manufacturing process as well. Gel may be poured or squirted into the gel registration fixture instead of using sheet gel. In this scenario, the gel would bond the sections directly to the tin. In yet another embodiment, the sections may be oriented annularly and not vertically.

Alternatively the dielectric backing layer may not be precut, but rather notched, and easily torn at the notches. In this embodiment, the tearing would then occur through the backing layer and through the metal layer. In yet another embodiment, the gel sections may be separated by large gaps or the gel sections may be placed in intimate contact with each other so that it makes electrical contact, but tears easily when required. Thus it is contemplated that after construction the gel assembly could be contiguous, integral or completely separated. In yet another embodiment, the gel sections could be connected by narrow gel sections, forming finger-like projections between two larger gel sections. The advantage of this construction is that the narrow gel sections are easily torn through when the metal layer is torn. These embodiments are ideally suited for use with a defibrillator where the user selects the desired energy level, making it a solution for the manual defibrillator user.

In another method of manufacturing the electrode shown in FIGS. 1 and 2, the electrode physically manufactured using the processes described above. However, the conductive portion of the electrode is divided into two or more sections with a separate wire electrically connecting each section to the defibrillator. As shown in FIG. 3, the wire 142. connecting a first pad section to the defibrillator are connected to an energy attenuator circuit located inside the defibrillator. The first pad section 122, represents the pediatric electrode pad section portion of the assembly. The wire 142' connecting a second pad 121 section to the defibrillator is non-attenuated and is parallel to the attenuated first line. Where appropriate a third pad section may be employed where it is desirable to achieve infant, child and adult electrode sizing. Importantly, more than two pad sections may be appropriate for a variety of reasons, including size of the patient, etc., and is not just limited to the concept of treating infants, children and adults. Additionally, in most embodiments, it is contemplated that the first pad section would have an area smaller than the second pad section, although such a size difference is not required to practice the invention.

In one method of operation, when entire pad, including first pad section and second pad section (or first, second and third, etc.) is used on an adult patient, the current will find the easiest path to ground. In this case, the easiest path would be to travel through the unattenuated line to the electrode pad. When the second pad section is separated from the rest of the pad, the electrical connection between the second section and the defibrillator is broken. As a result it appears as an open to the circuit, which causes the current to flow through the attenuated side of the loop and into the remaining electrode section. The electrical separation can occur either at the pad (as shown) or at the defibrillator interface. Alternatively, the electrical separation could also occur along the length of the leadwire, with a wire-to-wire connector, for example.

In yet another method of manufacturing an electrode assembly of this invention, a pad assembly which employs a dielectric release liner (shown in FIG. 3 as 146) divided into two or more sections is employed. The electrode pad assembly would be manufactured as described above, except that after the release liner is applied, a die is used to kiss-cut only through the release liner. Thus, the release liner is cut into separate sections while the gel, tin and backing layers remain in a single piece. Alternatively, the release liner can be precut prior to being applied to the gel. In yet another alternative, the release liner could be perforated for easy tearing away from the desired sections.

In yet another embodiment, the release liner can be die-cut into patterns. The patterns providing the benefit of reducing current densities at the edge of the electrodes.

As will be appreciated by those skilled in the art, the actual construction described above is provided by way of illustration only and should in no way limit the scope of the invention. Although described in terms of a disposable electrode pad, other constructions are possible. It is also contemplated that materials other than those described herein may be used without departing from the scope of the invention. Further it is within the scope of the invention to have a plurality of electrode elements.

FIG. 3 shows a cross-section of the electrode shown in FIG. 1, and which is assembled as described above. The backing layer 110 is adhered to the conductive layer 120 which is then covered by the gel layer 150. A release liner 146 is provided along the top of the gel layer. As discussed above, the release liner 146 may be pre-cut in order to allow the user to selectively remove portions of the release liner in order to obtain a desired surface area or pattern.

Figure 5A:
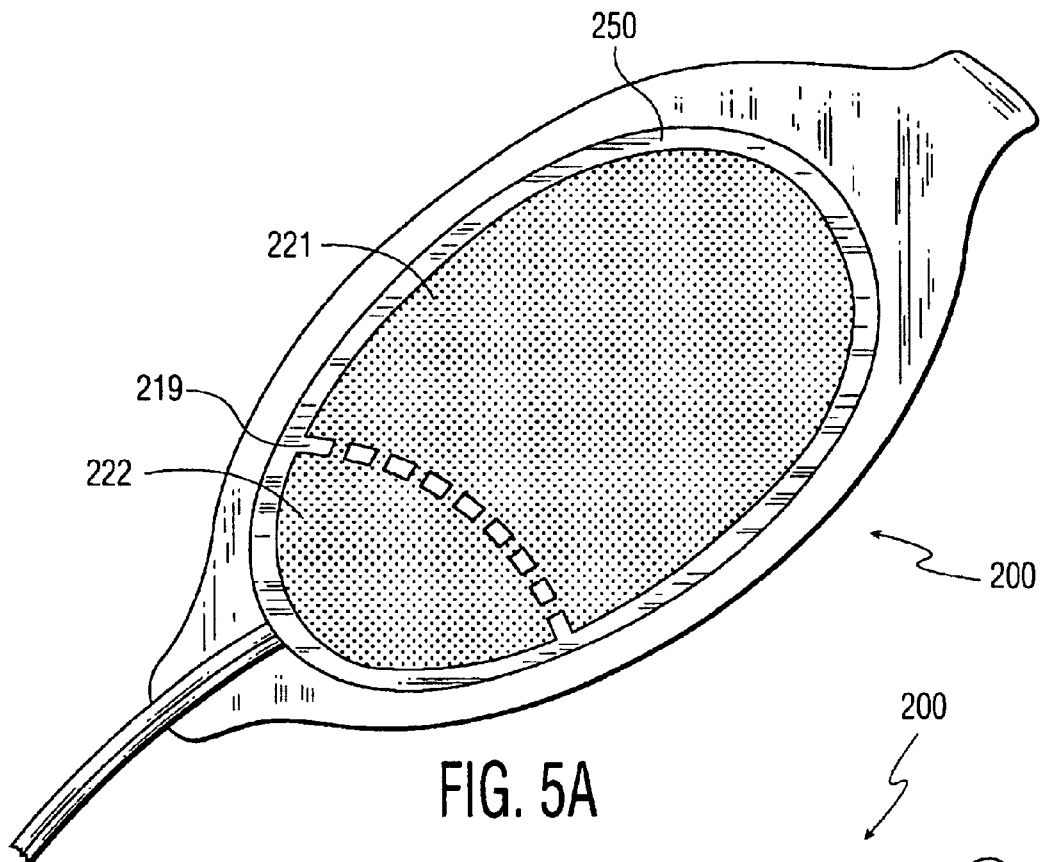
FIGS. 5a and 5b are bottom elevational views of an alternative embodiment of an electrode system according to a preferred embodiment wherein the conductive element has a series of perforations across a length which enable the electrode to be separated into a smaller electrode.

FIG. 5a is a bottom elevational view of an alternate embodiment of an electrode 200, according to this invention. The electrode 200 has a conductive element forming a primary contact area 222 and a secondary contact area 221. The size of the primary contact area 222 is such that it would be appropriate for delivering defibrillation therapy to a pediatric or infant patient. In this embodiment, the size of the primary contact area 222 in combination with the secondary contact area 221 is such that it would be appropriate for delivering defibrillation therapy to an adult patient. Other size combinations can be employed without departing from the scope of the invention. A gel layer 250 is also provided. The conductive element 220 features at least one perforated section across its length 219. The perforated section 219 enables the conductive element 220 to be separated into the primary contact area 222 and the secondary contact area 221. The perforations may be relatively large, e.g. wherein each perforation is 0.05 cm, or they may be very small. The relative size of the perforations is unimportant provided that the electrode 200 may be separated into the primary 222 and the second 221 elements.

Figure 5B:
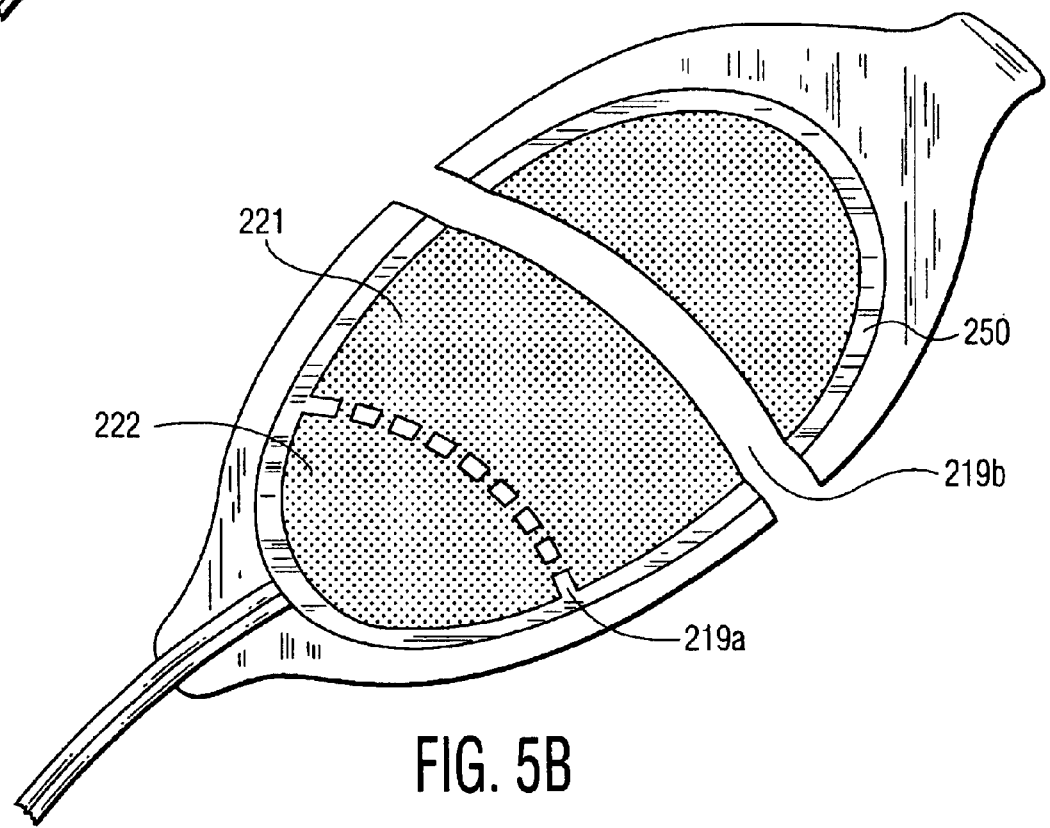

An alternative embodiment is shown in FIG. 5b. In this embodiment, the electrode 200 has a conductive element 220 forming a primary contact area 222, a secondary contact area 221 and a tertiary contact area 223. The size of the primary contact area 222 is such that it would be appropriate for delivering defibrillation therapy to an infant patient. The size of the primary contact area 222 in combination with the secondary contact 221 area is such that it would be appropriate for delivering defibrillation therapy to a pediatric patient. Finally, the size of the primary contact area 222 in combination with the secondary contact area 221 and the tertiary contact area 223 is such that it would be appropriate for delivering defibrillation therapy to an adult patient. A gel layer 250 is also provided.

The conductive element 220 features at least two perforated sections across its length 219a, 219b. The perforated sections 219a, 219b enable the conductive element 220 to be separated along the lines between either the primary contact area 222 and secondary contact area 221, or the secondary contact area 221 and tertiary contact area 223. As illustrated the first perforated section 219a has not been separated and the second perforated section 219b has been separated. As discussed above, the relative size of the perforations is unimportant provided that the electrode 200 may be separated into parts.

When the electrode pad 200 is deployed for defibrillation, the operator attaches an electrode pad to the patient's torso at each of either the anterior/anterior position or the anterior/posterior position.

As will be appreciated by those skilled in the art, many changes, modifications, variations and other uses and applications of the subject invention will, however, become apparent after considering this specification and the accompanying drawings which disclose preferred embodiments thereof. All such changes, modifications, variations and other uses and applications which do not depart from the spirit and scope of the invention are deemed to be covered by the invention, which is limited only by the claims which follow.

What is claimed:

1. A disposable medical electrode pad comprising:
   a conductive gel layer having two surfaces each with a surface area;
   a single, conductive layer that is separable across the conductive layer so as to form at least two sections comprising at least a first conductive electrode section having two surfaces each with a surface area wherein one surface of the first conductive electrode section is adhered to one surface of the conductive gel layer and a second conductive electrode section having two surfaces each with an surface area wherein one surface of the second conductive electrode section is adhered to one surface of the conductive gel layer;

respective conductors in communication with said sections comprising at least the first and second conductive electrode sections, wherein the conductors selectively deliver therapy through at least the first and second conductive electrode section, or both; and a dielectric layer.

2. The disposable medical electrode pad of claim 1 wherein the surface area of the first conductive electrode layer is less than 75 cm$^2$.

3. The disposable medical electrode pad of claim 1 wherein the surface area of the first conductive electrode layer is less than 50 cm$^2$.

4. The disposable medical electrode pad of claim 1 wherein the surface area of the second conductive electrode layer is less than 100 cm$^2$.

5. The disposable medical electrode pad of claim 1 wherein the surface area of the second conductive electrode layer is less than 75 cm$^2$.

6. The disposable medical electrode pad of claim 1 further comprising a third conductive electrode section in communication with the first and second conductive electrode sections.

7. The disposable medical electrode pad of claim 6 wherein the surface area of the third conductive electrode layer is less than 40 cm$^2$.

8. The disposable medical electrode pad of claim 6 wherein the third conductive electrode section is removable from the first and second conductive electrode sections.

9. The disposable medical electrode pad of claim 1 wherein the conductors are used for delivering pulses of electrical energy.

10. The disposable medical electrode pad of claim 9 wherein the pulses of electrical energy are used to cardiovert a patient.

11. The disposable medical electrode pad of claim 9 wherein the pulses of electrical energy are used to defibrillate a patient.

12. The disposable medical electrode pad of claim 1 wherein the first conductive electrode section is removable from the second conductive electrode section.

13. The disposable medical electrode pad of claim 1 wherein the conductive gel layer is contiguous.

14. The disposable medical electrode pad of claim 1 wherein the conductive gel layers is further comprised of a first gel section and a section gel section.

15. The disposable medical electrode pad of claim 1 wherein the conductive gel layer is perforated along a length.

16. The disposable medical electrode pad of claim 1 wherein the conductive gel layer is tearable along a length.

17. The disposable medical electrode pad of claim 1 wherein the dielectric layer is further comprised of a first dielectric layer and a second dielectric layer.

18. The disposable medical electrode pad of claim 1 wherein the dielectric layer is perforated along a length.

19. The electrode pad of the claim 1, wherein said conductive layer is non-concentrically separable across at least a longitudinal section of said conductive layer so that the at least two sections formed are asymmetrically-sized, the surface area of the first conductive section being less than 100 cm$^2$ and the surface area of the second conductive section being less than 150 cm$^2$.

20. A method of using a disposable medical electrode pad coupled to a defibrillator, comprising:

detecting the physiological size of a patient;

prior to applying the electrode pad to the patient, determining whether to remove a portion of a conductive electrode layer from an electrode pad to which multiple conductors are communicatively connected;

detaching the portion, including a conductor communicatively connected to the portion, based on the determination of whether to remove the portion;

applying to the patient the electrode pad from which said portion has been detached; and delivering from the defibrillator to the patient therapy through said electrode pad from which said portion has been detached.

21. The method of using a medical electrode pad of claim 20 further comprising the step of:

removing a portion of the conductive electrode layer from the electrode pad.

22. The method of using a medical electrode pad of claim 21 further comprising the step of delivering therapy to the patient, wherein the electrotherapy delivered is cardioversion.

23. The method of using a medical electrode pad of claim 21 further comprising the step of delivering therapy to the patient, wherein the electrotherapy delivered is defibrillation.

24. The method of using a medical electrode pad of claim 21 further comprising the step of delivering therapy to the patient, wherein the electrotherapy delivered is pacing.

* * * * *